(12) United States Patent
Tsukada et al.

(10) Patent No.: US 7,897,751 B2
(45) Date of Patent: Mar. 1, 2011

(54) PHARMACEUTICAL PREPARATION

(75) Inventors: Yusuke Tsukada, Hirakata (JP);
Hiroyuki Tsujimoto, Hirakata (JP);
Makoto Sakaguchi, Ibarak (JP)

(73) Assignee: Hosokawa Micron Corporation, Osaka (JP)

( * ) Notice: Subject to any disclaimer, the term of this patent is extended or adjusted under 35 U.S.C. 154(b) by 776 days.

(21) Appl. No.: 11/812,459

(22) Filed: Jun. 19, 2007

(65) Prior Publication Data

US 2009/0061007 A1 Mar. 5, 2009

(30) Foreign Application Priority Data

Aug. 31, 2006 (JP) ................. 2006-235153

(51) Int. Cl.
*C07H 21/04* (2006.01)
*C12Q 1/68* (2006.01)

(52) U.S. Cl. ............ 536/24.5; 435/6; 435/325; 435/375; 514/44

(58) Field of Classification Search ................... None
See application file for complete search history.

(56) References Cited

U.S. PATENT DOCUMENTS

| 5,674,192 | A | 10/1997 | Sahatjian et al. | |
|---|---|---|---|---|
| 6,200,304 | B1 | 3/2001 | Schrader | |
| 6,262,033 | B1 * | 7/2001 | Morishita et al. | 514/44 R |
| 7,550,441 | B2 | 6/2009 | Farokhzad et al. | |
| 2002/0133126 | A1 | 9/2002 | Schrader | |
| 2004/0162251 | A1 | 8/2004 | Morishita et al. | |
| 2006/0051426 | A1 | 3/2006 | Golomb et al. | |
| 2006/0241066 | A1 | 10/2006 | Tomita et al. | |

FOREIGN PATENT DOCUMENTS

| JP | 2006-28041 A | 2/2006 |
|---|---|---|
| JP | 2006-111591 | 4/2006 |
| WO | WO2008/139473 | 11/2008 |

OTHER PUBLICATIONS

Kumar et al. Biomaterials, 2004. 25:1771-1777.*
Wischke et al. Journal of Controlled Release, 2006. 114:359-368.*
Takeuchi, Hiromitsu et al., Bulletin of Gifu Pharmaceutical University, Jun. 30, 2005, vol. 54, p. 57-58.
Yamamoto, Hiromitsu et al., Design of Nanoparticle Carrier For Gene Delivery, Annual Report of Hosokawa Powder Technology Foundation, Japan, May 2006, No. 13, p. 17-25.
Munier, S. et al., Cationic PLA nanoparticles for DNA delivery: Comparision of three surface polications for DNA binding, protection and transfection properties, Colloid and Surfaces B: Biointerfaces, Jul. 10, 2005, vol. 43, No. 3-4, p. 163-173.
Tahara, Kohei et al., Design of Chitosan-Modified Polylactic Acid-Glycolic Acid Nanosphers Entrapping siRNA, Abstracts of Annual Meeting of the Pharmaceutical Society of Japan, Mar. 6, 2006, vol. 126th, No. 2, p. 86.
Tahara, Kohei et al., Design of Chitosan-Surface-Modified Polylactic Acid-Glycolic Acid Nanosphers for Delivery of siRNA and its Evaluation, Drug Delivery System, Jun. 2006, vol. 21, No. 3, p. 294.

* cited by examiner

*Primary Examiner* — James (Doug) Schultz
(74) *Attorney, Agent, or Firm* — Fitch, Even, Tabin & Flannery

(57) ABSTRACT

A pharmaceutical preparation comprises nano-level particles (nanospheres) of a biocompatible polymer having, as held on their surfaces, an NFκB decoy capable of binding to NFκB to inhibit its activity. With penetration of the nanoparticles inside cells, the NFκB decoy may be delivered to an affected site and the NFκB decoy may be released from the surfaces of the nanoparticles and may be thereby efficiently and specifically introduced into the affected site.

12 Claims, 5 Drawing Sheets

PHARMACEUTICAL PREPARATION

This Application is based on and claims the foreign priority benefit under 35 U.S.C. §119 from Japanese Patent Application No. 2006-235153, filed on Aug. 31, 2006, the complete disclosure of which, including sequence listing(s), is incorporated herein by reference.

BACKGROUND OF THE INVENTION

1. Field of the Invention

The present invention relates to a pharmaceutical preparation containing an NFκB decoy oligonucleotide that binds to NFκB.

2. Description of the Related Art

Recently, all base sequences of a human genome have been decoded, and it has become clarified that various diseases may be caused by genetic disorders, and in future, the relationship between more diseases and genes may be clarified. Based on these information, so-called Gene Therapy which enables various diseases caused by genetic disorders to be treated fundamentally at genetic level is now strongly anticipated as a new therapeutic strategy for intractable diseases.

For example, it is suggested that most of various diseases such as asthma, cancer, cardiac disease, aneurysm, autoimmune disease, viral infection, though individually exhibiting different symptoms, may be caused by abnormal expression (over-expression or under-expression) of one or a few proteins. In general, the protein expression is controlled by various transcriptional regulators such as transcriptional activators and transcriptional suppressors.

NFκB is a transcriptional regulator comprising p65 and p50 heterodimers. In general, NFκB exists in a cytoplasm as a form with its inhibitor IκB bonding thereto, and its nuclear import is thereby inhibited. However, when some stimulation such as cytokine, ischemia or reperfusion is given thereto for some reasons, IκB may be decomposed through phosphorylation and NFκB may be thereby activated, resulting in its nuclear import. The nuclear-imported NFκB binds to the NFκB-binding region on a genome, and promotes the transcription of the gene existing at its downstream. Some genes existing at the downstream of the NFκB-binding site are known, including, for example, inflammatory cytokines such as IL-1, IL-6, IL-8, tumor necrosis factor α (TNFα), and adhesion factors such as VCAM-1, ICAM-1.

Some reasons for atopic dermatitis, a type of intractable skin diseases may be taken into consideration, including environmental factors such as allergen, environmental pollution, pollen, stress, and genetic factors such as over-immune system, skin barrier disorder; and these factors may act compositely and the water-holding function and the barrier function of the skin horny layer (corneal layer of epidermis, stratum corneum epidermidis) may lower thereby resulting in that allergens and stimulants may invade the inside of the skin to cause irritation and itching. In addition, after repeatedly scratched, the skin horny layer may be damaged and allergens and stimulants may more readily invade the inside of the skin; and the vicious circle is repeated.

It is known that, in a pathology of atopic dermatitis or a model animal with atopic dermatitis, activation of NFκB induces expression of inflammation-related gene groups (e.g., cytokine, chemokine, adhesion factor) that accompany invasion or activation of lymphocytes, therefore playing an important role in disease onset and development. In addition, it is suggested that the activation of NFκB is an important mechanism also in skin diseases such as psoriasis vulgaris, contact dermatitis.

Recently, studies of administering an NFκB decoy oligodeoxynucleotide (hereinafter referred to as "NFκB decoy") capable of inhibiting the formation of cytokines and others that bind to NFκB to cause inflammations, thereby fundamentally removing causes of disease for atopic dermatitis and others, have been made actively.

For example, Patent References 1 to 3 disclose an ointment preparation for treatment of skin diseases such as atopic dermatitis, containing an NFκB decoy. Patent Reference 4 discloses a method of using a liposome as a carrier (vector) of NFκB decoy. Further, Patent Reference 5 discloses a method of incorporating a nucleic acid drug in folic acid-modified nanoparticles thereby increasing the intracellular transportation of the drug.

However, the NFκB decoy has an extremely large molecular weight of about 12,000; and according to the methods of Patent References 1 to 3, its skin permeability is low in a site eroded by scratching or except a facial site having a relatively low barrier function, and therefore it could not be transported to the inside of the cells in affected sites. Accordingly, at those sites having a high barrier function, the NFκB decoy could not sufficiently exhibit its therapeutical effect; and it is desired to further improve the skin permeability and the intracellular transportability of the NFκB decoy. In the method of Patent Reference 4, the liposome is a phospholipid and is highly safe to human bodies, but on the other hand, the method is insufficient in point of the efficiency and the effect of the NFκB decoy introduction and the sustainability thereof. Further, the method of Patent Reference 5 is problematic in that it requires an additional step of preparing folic acid-polyethylene glycol-distearoylphosphatidylethanolamine that is to be the starting material for the folic-acid modified nanoparticles, and the number of the constitutive steps of the method increases, therefore resulting in the increase in the production costs for the drug preparation.

SUMMARY OF THE INVENTION

In consideration of the above-mentioned problems, an object of the invention is to provide a quick-acting, highly-safe and easily-producible pharmaceutical preparation, capable of efficiently transporting the NFκB decoy therein into the inside of a skin even in the site thereof having a high barrier function.

In order to attain the above object, the invention provides a pharmaceutical preparation containing biocompatible polymer nanoparticles that are coated with a cationic polymer on their surfaces and have an NFκB decoy oligonucleotide adsorbed and held thereon.

According to this constitution, an NFκB decoy is held on the surface of nanoparticles formed of a biocompatible polymer, and there is provided a pharmaceutical preparation having high safety to human bodies and capable of efficiently transporting the NFκB decoy therein into the inside of cells owing to the high intravital permeability of the nanoparticles. In addition, in this case, the NFκB decoy on the surfaces of the nanoparticles may be released within a short period of time after administration, and therefore, as compared with a case where the NFκB decoy is included inside the nanoparticles, this is more advantageous in point of its quick-acting potency. Moreover, since the adsorbability of the nanoparticles to negatively-charged cell walls is increased, the delivery efficiency of the NFκB decoy held on the surfaces of the nanoparticles to the inside of cells may be increased. The nanoparticles to be used in the invention enable to be readily produced by coating their surfaces with a cationic polymer.

In the pharmaceutical preparation having the above constitution of the invention, the NFκB decoy oligonucleotide may be included inside the nanoparticles.

According to this constitution, in the pharmaceutical preparation having the above constitution, the NFκB decoy is additionally included inside the nanoparticles, and therefore, the NFκB decoy content in the pharmaceutical preparation may be increased and the NFκB decoy may be efficiently delivered to a targeted site, and in addition, the form of the pharmaceutical preparation maybe down-sized. Moreover, while the quick-acting potency of the pharmaceutical preparation is kept high owing to the NFκB decoy held on the surfaces of the nanoparticles, the NFκB decoy included inside the nanoparticles may be gradually released to thereby increase the long-lasting sustainability of the pharmaceutical preparation.

In the pharmaceutical preparation having the above constitution of the invention, the nanoparticles may be hybridized with a binder and the NFκB decoy oligonucleotide may be further included inside the outer layer formed of the binder.

According to this constitution, in the pharmaceutical preparation having the above constitution, the nanoparticles are hybridized with a binder and the NFκB decoy is further included inside the binder layer formed on the surfaces of the nanoparticles, and therefore, the amount of the NFκB decoy held by the surfaces of the nanoparticles could be increased. Further, owing to the hybridization, the handlability of the nanoparticles may be improved.

In the pharmaceutical preparation having the above constitution of the invention, the cationic polymer may be chitosan or a chitosan derivative.

According to this constitution, in the pharmaceutical preparation having the above constitution, a biodegradable chitosan or chitosan derivative is used as the cationic polymer, and therefore negative influences of the pharmaceutical preparation of this embodiment on living bodies may be reduced more and the safety thereof is thereby increased.

In the pharmaceutical preparation having the above constitution of the invention, the biocompatible polymer may be any of a polylactic acid, a polyglycolic acid or a lactic acid/glycolic acid copolymer.

According to this constitution, in the pharmaceutical preparation having the above constitution, the biocompatible polymer is any of a polylactic acid, a polyglycolic acid, or a lactic acid/glycolic acid copolymer, and therefore, the stimulation and the toxicity of the pharmaceutical preparation to living bodies may be low and the pharmaceutical preparation may safely contain the NFκB decoy therein, and in addition, the pharmaceutical preparation may be stored for a long period of time while it may keep the potency of the NFκB decoy therein as such, and moreover, the pharmaceutical preparation may slowly release the NFκB decoy therein owing to the degradation of the biocompatible polymer.

In the pharmaceutical preparation having the above constitution of the invention, the NFκB decoy oligonucleotide may include an NFκB-binding sequence (this may be referred to as "consensus sequence") represented by the following SEQ ID NO: 1.

```
[G]nGGRHTYYHC         (SEQ ID NO: 1)
```

(wherein n indicates 0 or 1; R means A or G; Y means C or T; H means A, C or T).

According to this constitution, the pharmaceutical preparation having the above constitution comprises the NFκB decoy including the NFκB-binding sequence represented by the general formula (1), and therefore, the pharmaceutical preparation may prevent NFκB from binding to the intrinsic binding site on a genome to thereby effectively prevent the formation of cytokines and others and the generation of inflammations caused by them.

In the pharmaceutical preparation having the above constitution of the invention, the NFκB decoy oligonucleotide may include at least one of GGGATTTCCC (SEQ ID NO: 2), GGGACTTTCC (SEQ ID NO: 3) or GGACTTTCC (SEQ ID NO: 4), as the NFκB-binding sequence.

According to this constitution, in the pharmaceutical preparation having the above constitution, the NFκB decoy oligonucleotide may include at least one of GGGATTTCCC (SEQ ID NO: 2), GGGACTTTCC (SEQ ID NO: 3) or GGACTTTCC (SEQ ID NO: 4) as the NFκB-binding sequence, and therefore, the bindability of NFκB the pharmaceutical preparation is bettered.

In the pharmaceutical preparation having the above constitution of the invention, the NFκB decoy oligonucleotide may be a double-stranded oligonucleotide comprising a sequence 5'-CCTTGAAGGGATTTCCCTCC-3' (SEQ ID NO: 5) and a sequence complementary to it, 5'-GGAGGGAAATCCCTTCAAGG-3' (SEQ ID NO: 6).

According to this constitution, in the pharmaceutical preparation having the above constitution, the NFκB decoy oligonucleotide may be a complementary double-stranded oligonucleotide comprising a sequence 5'-CCTTGAAGGGATTTCCCTCC-3' (SEQ ID NO: 5) and a sequence 5'-GGAGGGAAATCCCTTCAAGG-3' (SEQ ID NO: 6), and therefore, NFκB may more favorably bind to the pharmaceutical preparation of this type.

In the pharmaceutical preparation having the above constitution of the invention, the content of the NFκB decoy oligonucleotide in the nanoparticles may be from 0.5% by weight to 30% by weight.

According to this constitution, in the pharmaceutical preparation having the above constitution, the content of the NFκB decoy in the nanoparticles may be from 0.5% by weight to 30% by weight. In this case, the content of the NFκB decoy may be suitably so designed that the increase in the particle size of the nanoparticles may be prevented while the amount of the nanoparticles to be in the preparation is suitably controlled.

In the pharmaceutical preparation having the above constitution of the invention, the nanoparticles may have a mean particle size of from 10 nm to 1,000 nm.

According to this constitution, in the pharmaceutical preparation having the above constitution, the nanoparticles may have a mean particle size of from 10 nm to 1,000 nm. Accordingly, the nanoparticles delivered to a targeted site may be more readily taken inside cells, and the preparation may realize a higher genetic expression efficiency. In addition, when the pharmaceutical preparation is used for percutaneous administration, it realizes high percutaneous permeation and absorption.

In the pharmaceutical preparation having the above constitution of the invention, the nanoparticles may have a mean particle size of from 50 nm to 300 nm.

According to this constitution, in the pharmaceutical preparation having the above constitution, the nanoparticles may have a mean particle size of from 50 nm to 300 nm. Accordingly, when the pharmaceutical preparation is used for percutaneous administration, it realizes extremely higher percutaneous permeation and absorption.

The pharmaceutical preparation having the above constitution of the invention may be used for treatment of skin diseases.

According to this constitution, the pharmaceutical preparation having the above constitution is used for treatment of skin diseases, and owing to the skin-permeable effect of the nanoparticles and the cell wall-adsorptive effect thereof, the pharmaceutical preparation may exhibit an excellent therapeutical effect for skin diseases.

The skin disease for which the pharmaceutical preparation having the above constitution of the invention may be used may be atopic dermatitis.

According to this constitution, in the pharmaceutical preparation having the above constitution, the pharmaceutical preparation having the above constitution of the invention may be used for atopic dermatitis as a type of skin diseases, and the invention thus provides an excellent therapeutical method for atopic dermatitis, a type of intractable diseases.

DESCRIPTION OF THE PREFERRED EMBODIMENTS

Figure 1:
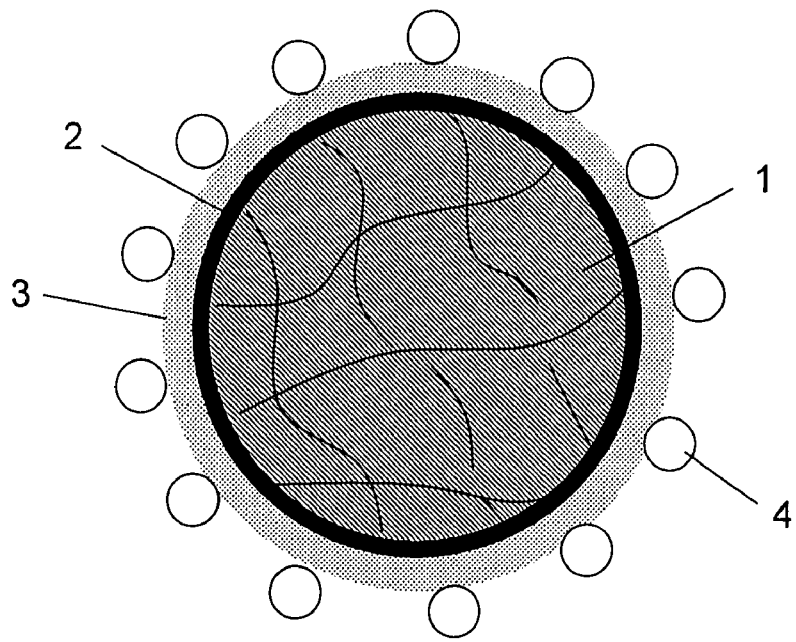
FIG. 1 is a schematic view showing a structure of a nanosphere where an NFκB decoy is electrostatically held on the surface of the particle.

The biocompatible nanoparticles for use in the pharmaceutical preparation of the invention are particles of a biocompatible polymer having a nano-level size (nanospheres), and these have a nucleic acid compound, NFκB decoy held on their surfaces. When the nanoparticles are penetrated inside a living body, then the NFκB decoy may be delivered to an affected site and the NFκB decoy may be released from the surfaces of the nanoparticles, and therefore, they may be favorably used as a material for a pharmaceutical preparation.

The NFκB decoy to be the pharmaceutical component of the pharmaceutical preparation of the invention competes with the binding region on a genome to which NFκB binds, therefore acting as a decoy selectively binding to NFκB.

"Decoy" as referred to in this description is meant to indicate a so-called "decoy molecule" having a structure similar to that of the binding region on a genome to which naturally a transcription factor is to bind. In the presence of the decoy, a part of the transcription factor does not bind to the binding region on a genome to which naturally it is to bind, but binds to that decoy that functions as a "decoy" for the binding region. Accordingly, the number of the molecules of the transcription factor to bind to the intrinsic binding region decreases and the activity of the transcription factor may be thereby reduced.

As the decoy, generally used is an oligonucleotide constructed by bonding a nucleotide to both ends of the binding sequence represented by the above-mentioned SEQ ID NO: 1. The nucleotide part at both ends of the binding sequence may be referred to as an additional sequence, and it comprises at least one base, preferably from 1 to 20 nucleotides, more preferably from 1 to 10 nucleotides, much more preferably from 1 to 7 nucleotides. Not specifically limited, the full chain length of the decoy may comprise generally from 15 to 35 nucleotides, preferably from 16 to 30 nucleotides, more preferably from 17 to 25 nucleotides.

The NFκB decoy may be a double-stranded oligonucleotide containing at least one binding sequence of NFκB. Preferably, the double-strand is a completely complementary sequence. Specifically, one typical NFκB decoy structure is a double-stranded oligonucleotide that comprises a sense chain oligonucleotide having a constitution of 5'-5' terminal flanking sequence-binding sequence-3' terminal flanking sequence-3', and an antisense chain oligonucleotide complementary to it.

Even though containing at least one (generally, one or two pairs) noncomplementary base pair, it may be within the scope of the NFκB decoy as referred to in this description, so far as it may bind to NFκB. Further, a double-stranded oligonucleotide having plural transcription factor-binding sites, where plural binding sites are linked to each other directly in tandem or via one or a few nucleotides sandwiched therebetween, between the 5'-terminal flanking sequence and the 3'-terminal flanking sequence may also be mentioned as another constitution of the NFκB decoy.

Furthermore, even a single-stranded oligonucleotide, or that is, a so-called ribbon-type decoy or a staple-type decoy which has a binding sequence and a complementary sequence to it in the molecule and in which these form a double-stranded structure in the molecule may also be within the scope of the NFκB decoy as referred to in this description so far as NFκB may bind to it.

The binding sequence of NFκB is described in various references (for example, Non-Patent Reference 6), and one concrete binding sequence may be represented by the following SEQ ID NO: 1.

[G]nGGRHTYYHC         (SEQ ID NO: 1)

(wherein n indicates 0 or 1; R means A or G; Y means C or T; H means A, C or T).

Concretely, for example, it includes GGGATTTCCC (SEQ ID NO: 2), GGGACTTTCC (SEQ ID NO: 3) or GGACTTTCC (SEQ ID NO: 4), to which, however, the invention should not be limited.

Preferred examples of the NFκB decoy for use in the invention are a double-stranded oligonucleotide comprising a sequence 5'-CCTTGAAGGGATTTCCCTCC-3' (SEQ ID NO: 5) and its complementary sequence, 5'-GGAGGGAAATCCCTTCAAGG-3' (SEQ ID NO: 6); a double-stranded oligonucleotide comprising a sequence 5'-AGTTGAGGACTTTCCAGGC-3' (SEQ ID NO: 7) and its complementary sequence, 5'-GCCTGGAAAGTCCTCAACT-3' (SEQ ID NO: 8); and a double-stranded oligonucleotide comprising a sequence 5'-AGTTGAGGGGACTTTCCCAGGC-3' (SEQ ID NO: 9) and its complementary sequence, 5'-GCCTGGGAAAGTCCCCTCAACT-3' (SEQ ID NO: 10).

For producing method of the NFκB decoy for use in the invention, employable is a nucleic acid synthesis method generally used in genetic engineering. For example, it may be directly produced, using a DNA synthesis apparatus; or an oligonucleotide or a part of it may be first produced and then it may be amplified according to a PCR method or a cloning vector method. Further, the oligonucleotide obtained according to these methods may be cleaved with a restriction endonuclease, or may be ligated using a DNA ligase, thereby producing the NFκB decoy.

The NFκB decoy for use in the invention may have at least one modified bond or nucleic acid. The modified bond includes, for example, phosphorothioate, methylphosphate, phosphorodithioate, phosphoramidate, boranophosphate, methoxyethylphosphate, morpholinophosphoramidate; and the modified nucleic acid includes, for example, peptide nucleic acid (PNA), locked nucleic acid (LNA), and nucleic acids having a modified, for example, dinitrophenylated (DNPated) or O-methylated base. Among of the above-mentioned bonds, more preferred is phosphorothioate.

DNPation and O-methylation is generally modification for ribonucleoside (RNA), however in the invention, the deoxyribonucleotide (DNA) to be modified in the oligonucleotide may be modified in the same manner as in RNA, in such a manner that an oligonucleotide is first synthesized and then the base therein is modified.

Whether the oligonucleotide to be the decoy or a decoy candidate may bind to a transcription factor could be confirmed in a binding activity test. The binding activity test of the NFκB decoy for its ability to bind to NFκB may be readily carried out, for example, using TransAM NFκB p65 Transcription Factor Assay Kit (trade name by ACTIVE MOTIF) and according to the instructions attached to the kit or through protocol modification daily made by those skilled in the art.

For producing method of the nanoparticles for use in the invention, employable is any method capable of processing the NFκB decoy and biocompatible molecules into particles having a mean particle size of less than 1,000 nm, with no specific limitation thereon. For it, preferably employed is a sphere crystallization method. The sphere crystallization method comprises controlling the crystal-forming and growing process in the final stage of compound production, thereby specifically designing spherical crystal particles of the compound, and processing the compound with directly controlling the physical properties thereof. One embodiment of the sphere crystallization method is an emulsion solvent diffusion method (ESD method).

The ESD method is a technique of producing nanospheres (nanoparticles) based on the principle mentioned below. In this method, used are two solvents. One is a good solvent capable of dissolving lactic acid/glycolic acid copolymer (PLGA) to be a base polymer for including a drug therein; and the other is, contrary to the former, a poor solvent not dissolving PLGA. The good solvent may be an organic solvent such as acetone capable of dissolving PLGA and miscible with the poor solvent. For the poor solvent, generally used is an aqueous polyvinyl alcohol solution.

The process is as follows: First, PLGA is dissolved in a good solvent, and a drug solution is added to and mixed with the good solvent so as not to precipitate PLGA therein. The mixture containing PLGA and the drug is dropwise added to a good solvent with stirring, whereupon the good solvent (organic solvent) in the mixture rapidly diffuses and moves into the poor solvent. As a result, the good solvent is self-emulsified in the poor solvent thereby forming submicron-size, good solvent emulsion droplets therein. Further, owing to the mutual diffusion of the good solvent and the poor solvent, the organic solvent continuously diffuses out of the emulsion into the poor solvent whereby the solubility of PLGA and the drug in the emulsion droplets lowers and finally, drug-containing spherical crystal particles, PLGA nanospheres are thus formed (this is a step of forming nanoparticles).

According to the above-mentioned sphere crystallization method, nanoparticles are formed physicochemically and the obtained nanoparticles are nearly spherical. In the method, therefore, homogeneous nanoparticles may be easily formed, not requiring the necessity of considering the problem of the remaining catalyst and starting compound in the product. After that, the good solvent, organic solvent is evaporated under reduced pressure (solvent evaporation step) to obtain a powder of nanoparticles. Then, the obtained powder may be used as it is, or, if desired, it may be freeze-dried and hybridized (hybridization step) to give hybridized particles.

Not specifically defined, the type of the good solvent and that of the poor solvent may be suitably determined depending on the type of the targeted drug. However, since the nanoparticles are used as a material of a medical preparation to be directly administered to human bodies, the solvents must be highly safe to human bodies and their environmental load must be low. As the poor solvent of the type, for example, preferred is an aqueous polyvinyl alcohol solution. Other surfactants than polyvinyl alcohol include lecithin, hydroxymethyl cellulose, hydroxypropyl cellulose.

The good solvent may be a low-boiling-point organic solvent, including halogenoalkanes, acetone, methanol, ethanol, ethyl acetate, diethyl ether, cyclohexane, benzene, toluene. For example, acetone alone having few negative influences on the environment and human bodies, or a mixed liquid of acetone and ethanol is preferred. In case where excess polyvinyl alcohol has remained in the product, a step of removing polyvinyl alcohol through centrifugation (removing step) may be provided after the solvent evaporation step.

The concentration of the aqueous polyvinyl alcohol solution may be suitably determined depending on the particle size of the spherical crystals to be granulated (nano-order in the invention). When the concentration of the aqueous polyvinyl alcohol solution is higher, then the adhesion of polyvinyl alcohol to the surfaces of the nanoparticles may be better, and the re-dispersibility in water of the dried nanoparticles may be improved; but on the other hand, when the concentration of the aqueous polyvinyl alcohol solution exceeds a predetermined level, then the viscosity of the poor solvent may increase and may have some negative influences on the diffusibility of the good solvent. Accordingly, though varying depending on the degree of polymerization or the degree of saponification of polyvinyl alcohol, the concentration may be preferably from 0.1% by weight to 10% by weight, more preferably 2% by weight or so, in case where a removing step is provided after the nanoparticles-forming step. However, in case where the removing step is not provided, then the concentration may be preferably at most 0.5% by weight.

The nanoparticles obtained in the manner as above may be hybridized into re-dispersible, aggregated nanoparticles (nano-composites) while they are powdered by freeze-drying treatment. In this case, an organic or inorganic substance may be used as a binder to hybridize the nanoparticles into re-dispersible nano-composites, and may be dried along with the nanoparticles. For example, the nanoparticles may be hybridized with glycoalcohol or saccharide, whereby the drug inclusion fluctuation therein may be effectively prevented and, in addition, glycoalcohol and the like may serve as a vehicle (binder) to improve the handlability of the resulting nanoparticles. The glycoalcohol includes mannitol, sorbitol, erythritol; and the saccharide includes trehalose, maltitose, xylitose. Of those, especially preferred is trehalose.

Through the hybridization, the nanoparticles are aggregated to form easily-handlable aggregated particles before using them; and when brought into contact with water in using them, they are restored to their original nanoparticles thereby exhibiting their characteristics such as high reactivity. For hybridizing the nanoparticles, preferably used is a freeze-drying method. If desired, the nanoparticles may be hybridized according to a fluidized-bed drying and granulation method. In particular, when a spray-drying type fluidized-bed granulation method where a mixture of the materials to be formed in to particles is sprayed into a fluidized gas is used as the fluidized bed drying and granulation method, then the time and labor-consuming freeze-drying step may be omitted and the intended hybridized particles may be readily formed within a short period of time, and the method is advantageous for industrial use.

When a weakly-crystalline saccharide or glycoalcohol is used as the binder in the spray-drying type fluidized-bed granulation method, then it may become amorphous during hybridization and could not favorably produce particles. Accordingly, highly-crystalline mannitol is preferably used.

Next, a method of adhering a NFκB decoy to the surfaces of the nanoparticles is described. Herein employed is an electrostatic adhesion method where a NFκB decoy is electrostatically held on the surfaces of the nanoparticles while the nanoparticles are hybridized through freeze-drying treatment. In order that the NFκB decoy that exists as an anionic molecule in an aqueous solution is electrostatically held on the surfaces of the nanoparticles, the surfaces of the nanoparticles must be so charged that they have a positive zeta potential.

In general, many particles dispersed in a liquid are positively or negatively charged, and a so-called diffusive electric double layer composed of a layer (fixed layer) of ions charged oppositely to the particle and strongly attracted to the particle surface, and a layer existing outside it (diffusive layer) is formed thereon, and it may be presumed that a part of the inside of the diffusive layer and the fixed layer may move along with the particles.

The zeta potential is a potential on the surface to cause the above movement (slide surface), based on the potential in an electrically neutral region sufficiently separated from the particles. When the absolute value of the zeta potential increases, then the repulsive force between the particles may increase and the stability of the particles may increase. On the contrary, when the zeta potential is nearer to 0, then the particles may more readily aggregate together. Accordingly, the zeta potential may be used as an index of the dispersion condition of particles.

In the step of forming the nanoparticles, when a cationic polymer is added to the poor solvent, then the surfaces of the formed nanoparticles may be modified (coated) with the cationic polymer and the zeta potential of the particle surface may be positive. With that, when an NFκB decoy is added while the nanoparticles are hybridized through freeze-drying treatment, then a predetermined amount of the NFκB decoy having formed negatively-charged anionic particles in the aqueous solution may be held on the surfaces of the nanoparticles owing to their electrostatic mutual effect.

The cell walls in a living body is negatively charged, and the surfaces of the nanoparticles produced according to a conventional sphere crystallization method generally has a negative zeta potential; and therefore, there is a problem in that the cell adhesiveness of the nanoparticles is poor owing to their electric repulsive force. Accordingly, charging the nanoparticle surfaces to have a positive zeta potential by the use of a cationic polymer as in the invention is favorable from the viewpoint of increasing the adhesiveness of the nanoparticles to the negatively-charged cell walls and of improving the intracellular mobility of the NFκB decoy.

A structure of a nanoparticle with NFκB decoys electrostatically held on the particle surface is shown in FIG. 1. The surface of the biocompatible nanoparticle 1 is coated with a polyvinyl alcohol 2, and is further coated with a cationic polymer 3 outside it, and the nanoparticle 1 therefore has a positive zeta potential owing to the cationic polymer 3. The NFκB decoys 4 are electrostatically held on the surface of the nanoparticle 1.

In case where a step of removing excess polyvinyl alcohol through centrifugation is provided before the freeze-drying treatment, then there may be a possibility that the cationic polymer may be partly removed along with polyvinyl alcohol. Accordingly, it is desirable to provide a step of again dipping the nanoparticles in a cationic polymer solution after the removing step.

The cationic polymer includes chitosan and chitosan derivatives; cationated celluloses prepared by bonding plural cationic groups to cellulose; polyamino compounds such as polyethyleneimine, polyvinylamine, polyallylamine; polyamino acids such as polyornithine, polylysine; polyvinyl imidazole, polyvinylpyridinium chloride, alkylaminomethacrylate quaternary salt polymer (DAM), alkylaminomethacrylate quaternary salt/acrylamide copolymer (DAA); cationic polymer prepared by bonding a cationic group such as a quaternary ammonium salt to a polymer whose constitutive unit is 2-methacryloyloxyethylphosphorylcholine (MPC) having both a phospholipid polar group (phosphorylcholine group), which is a constitutive component of a cell membrane (biomembrane), and a highly-polymerizable methacryloyl group (for example, copolymer of MPC and 2-hydroxy-3-methacryloyloxypropyltrimethylammonium chloride). In particular, chitosan and its derivatives are preferred.

Chitosan is a natural polymer with a large number of molecules of glucosamine, a type of amino group-having saccharide, and it is contained in the shells of lobsters, crabs, insects. It has characteristics of emulsion stability, shape retentivity, biodegradability, biocompatibility and antimicrobial capability, and is therefore widely used as materials for cosmetics, foods, clothing, medicines, etc. When chitosan is added to the poor solvent solution, then nanoparticles are obtained, that have a positive zeta potential and are highly safe, not having negative influences on living bodies.

When a more highly cationic one of cationic polymers is used, then the resulting nanoparticles may have a higher positive zeta potential, and therefore more NFκB decoys may be held on the particle surfaces with the result that the repulsive force of the particles increases and the stability of the particles is higher. For example, a part of chitosan that is naturally cationic is quaternated, then it may be a chitosan derivative (cationic chitosan) having a higher cationic potency, such as N-[2-hydroxy-3-(trimethylammonio)propyl]chitosan chloride, and this is favorably used in the invention. Further, chitosan and chitosan derivatives includes succinyl chitosan, succinyl carboxymethyl chitosan, chitosan pyrrolidone carboxylate, hydroxypropyl chitosan, chitosan lactate, glyceryl chitosan, or chitosan and derivatives of which hydroxyl group or amino group is converted into other various functional groups. The degree of de-acetylation of chitosan may be more than 50% preferably, more than 70% more preferably. The viscosity of chitosan may be more than 1 mPa s (0.5 wt %, 20° C.) preferably, more than 1 mPa s (0.5 wt %, 20° C.) not more than 1500 mPa s (0.5 wt %, 20° C.) more preferably.

When producing NFκB decoy-including nanoparticles is tried according to a conventional sphere crystallization method, then the water-soluble NFκB decoy dispersed and mixed in the good solvent may leak out and dissolve in the poor solvent, may be thereby inhibited.

Figure 2:
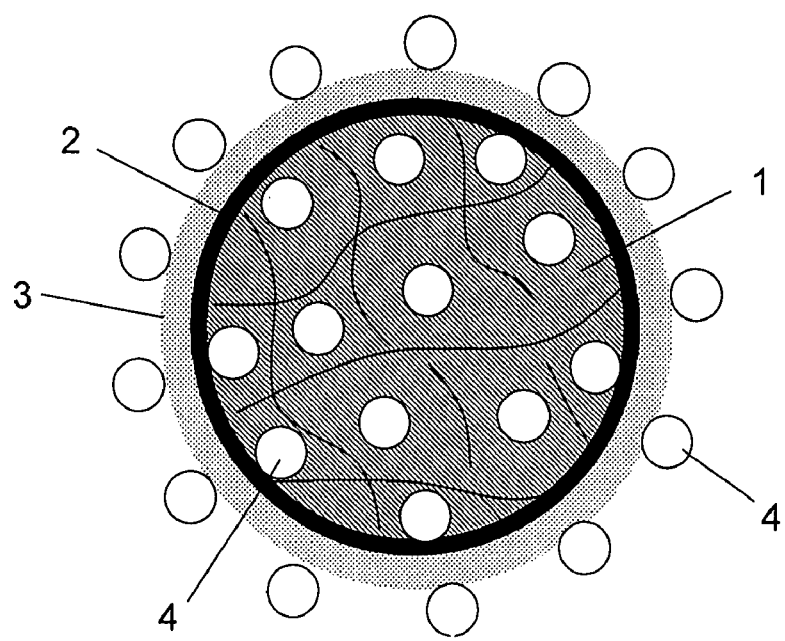
FIG. 2 is a schematic view showing a structure of a nanosphere where an NFκB decoy is electrostatically held on the surface of the particle and it is further included inside the particle.

A structure of a nanoparticle on which NFκB decoys are electrostatically held on the particle surface and are additionally included inside the particle is shown in FIG. 2. The NFκB decoys 4 are electrostatically held on the surface of the nanoparticle 1 coated with a cationic polymer 3, and are included inside the nanoparticle 1. Accordingly, the total content of NFκB decoys, which are extremely difficult to include inside nanoparticles, inside the nanoparticle and on the surface thereof may be increased. In addition, apart from the NFκB decoys to be released out from the surfaces of the nanoparticles immediately after their administration, other NFκB decoys may be gradually released out of the inside of the nanoparticles and may be active, and therefore, the pharmaceutical preparation comprising the nanoparticles of the type may satisfy both quick-acting capability and sustainability.

In this case, any other drug component that differs from the NFκB decoy in point of the potency and the action mechanism may be dissolved in the good solvent, and one or more such drug components may be included inside the nanoparticles. The pharmaceutical preparation of the type may be expected to exhibit promoted drug potencies owing to the synergistic effect of the NFκB decoy and the additional drug component.

For improving the affinity and the dispersion stability of the NFκB decoy in the good solvent, a cationic lipid such as N-[1-(2,3-dioleoyloxy)propyl]-N,N,N-trimethylammonium salt (DOTAP) may be added to the good solvent, thereby forming a composite with the NFκB decoy in the solvent. However, since the cationic lipid released inside cells may cause cytotoxicity, and special attention should be paid to its amount to be added.

When the nanoparticles are hybridized with a binder, the NFκB decoy may be included inside the outer layer formed of the binder. Accordingly, the amount of the NFκB decoy held on the surfaces of the nanoparticles may be further increased.

The biocompatible polymer for use in the invention is preferably a biodegradable one which is less stimulative and less toxic to living bodies, which is biocompatible and which may be degraded and metabolized after administration. Also preferably, the polymer particles may keep and gradually release the NFκB decoy held on their surfaces or included inside them. The material of the type includes polylactic acid (PLA), polyglycolic acid (PGA), lactic acid/glycolic acid copolymer (PLGA). PLGA is especially preferred. PLGA nanoparticles may include NFκB decoys inside them, and may be stored for a long period of time while keeping the NFκB decoy potency as such.

The evaluation of the carrier in a technique of efficiently delivering a drug to the targeted tissue/organ, or that is, a so-called drug delivery system (hereinafter referred to as DDS) is determined depending on the reach to cells, the intake into cells and the effect expression inside cells. Regarding the intake into cells, fusogenic liposomes have a highest intake ratio, and when the surfaces of the PLGA nanoparticles are modified with a cationic polymer, then the intake ratio thereof may be increased to the same level as that of liposomes. For application to percutaneous preparations to be directed to skin diseases such as atopic dermatitis, a liposome that is a liquid dispersion-type particle coated with a double lipid membrane is unsuitable since it could hardly penetrate through a skin barrier while keeping its structure and morphology and since it could hardly keep its structure in a preparation that comprises various components. On the other hand, PLGA nanoparticles are solid dispersion-type particles, and even for the above application, they are suitable since they can efficiently deliver the drug to the depth of the skin while keeping their structure. Further, because of the characteristics PLGA in point of the hydrolyzability and the long half-value period thereof, the PLGA nanoparticles may gradually release the drug within a few days to a month or more. From these characteristics thereof, the PLGA nanoparticles may be an excellent carrier in DDS.

Preferably, the molecular weight of PLGA is within a range of from 5,000 to 200,000, more preferably from 15,000 to 25,000. The compositional ratio of lactic acid to glycolic acid may be from 1/99 to 99/1, but preferably the ratio of lactic acid to glycolic acid is 1/0.333. PLGA having a content of lactic acid and glycolic acid of from 25% by weight to 65% by weight is amorphous and is soluble in an organic solvent such as acetone, and is favorably used herein.

Preferably, the surface of PLGA is modified with polyethylene glycol (PEG), as the affinity of PLGA to a water-soluble nucleic acid compound is improved, thereby facilitating the inclusion of the compound in the PLGA nanoparticles. PLGA may have a charging group or a functionalizable group such as an amino acid.

Apart from those mentioned in the above, other biocompatible polymers usable herein are polyalkylenes such as polyethylene, polypropylene; polyvinyl compounds such as polyvinyl alcohols, polyvinyl ethers, polyvinyl esters; polyamides, polycarbonates, polyethyleneglycol, polyethylene oxide, polyethylene terephthalate, acrylic acid/methacrylic acid polymer, cellulose and other polysaccharides; peptides, proteins; and their copolymers and mixtures.

In case where NFκB decoys are included inside the nanoparticles in addition to being held on the surfaces thereof, the ratio of the NFκB decoys to be held on the surfaces to those to be included inside them may be suitably determined depending on the degree of the required quick-acting capability and sustainability of the pharmaceutical preparation. Specifically, for the preparation that is required to express its effect immediately after its administration, the ratio of the NFκB decoys held on the surfaces of the nanoparticles may be higher. On the other hand, for the preparation that is required to be sustainable for a long period of time after its administration, the ratio of the NFκB decoys included inside the nanoparticles may be higher.

The content of the NFκB decoy in the nanoparticles is preferably higher since the amount of the nanoparticles to be in the pharmaceutical preparation may be lower. However, the amount of the NFκB decoys capable of being held on the surfaces of the nanoparticles is limited. In addition, when the NFκB decoys are included inside the nanoparticles, the particle size of the nanoparticles shall be large in proportion to the ratio of the NFκB decoy inclusion owing to the reason in producing them, and therefore, it may be difficult to deliver the nanoparticles to the depth of a living body. Accordingly, the total content of the NFκB decoys to be held on and included in the nanoparticles is preferably from 0.5% by weight to 30% by weight.

The amount of the NFκB decoy to be adhered to the surfaces of the nanoparticles may be varied by controlling the type and the amount of the cationic polymer to be added and by controlling the amount of the NFκB decoy to be added during freeze-drying treatment. The amount of the NFκB decoy to be added during freeze-drying treatment is preferably from 0.001 to 1.0 in terms of the ratio thereof by weight to the biocompatible polymer. When the weight ratio of the NFκB decoy to the biocompatible polymer is less than 0.001, then the concentration of the NFκB decoy may be too low and the ratio of the NFκB decoy adhering to the surfaces of the nanoparticles may be low; but when the weight ratio is more than 1.0, then the weight may be greatly larger than the limit of the amount of the NFκB decoy capable of being electrostatically held on the surfaces of the nanoparticles, therefore resulting in that much excess NFκB decoy not adsorbed by the surfaces of the nanoparticles may remain to lower the NFκB decoy adhesion efficiency.

On the other hand, the amount of the NFκB decoy to be included inside the nanoparticles may be varied, by controlling the amount of the NFκB decoy, the type and the amount of the cationic polymer to be added in formation of the nanoparticles, and by suitably selecting the type of the biocompatible polymer to form the nanoparticles. The amount of the NFκB decoy to be mixed in an organic solvent in forming the nanoparticles is preferably from 0.001 to 1.0 in terms of the ratio by weight to the biocompatible polymer. When the ratio by weight to the biocompatible polymer is less than 0.001, then the concentration of the NFκB decoy in the good solvent may be too low and the NFκB decoy inclusion inside the nanoparticles may lower; but when the ratio is more than 1.0, then the dispersibility of the NFκB decoy in the good solvent may be poor and the NFκB decoy inclusion relative to the amount thereof may lower.

Not specifically defined, the biocompatible nanoparticles produced in the invention may be any ones having a mean particle size of less than 1,000 nm; however, for introducing the NFκB decoy into the targeted site, the nanoparticles must be taken inside cells. For increasing the penetrability of the nanoparticles into the targeted cells, it is desirable that the mean particle size is at most 500 nm, more preferably from 50 nm to 300 nm.

In particular, for percutaneous administration, the particle size is preferably at most 100 nm in order that the nanoparticles delivered to the targeted site may be taken into cells through endocytosis of the cell membranes and may realize high genetic expression efficiency. In general, skin cells may have a size of 15,000 nm, and the skin cell spacing may be about 70 nm though varying in the shallow site and the deep site of skin; and therefore, when the mean particle size of the nanoparticles is at most 100 nm, then the penetrability of the nanoparticles into skin may be extremely high.

With the increase in the concentration of the cationic polymer in the poor solvent, the zeta potential of the surfaces of the nanoparticles may increase and the particle size of the nanoparticles may be thereby larger. In order to make the anionic NFκB decoy electrostatically held on the surfaces of the nanoparticles and to increase the adhesiveness of the nanoparticles to cells, the zeta potential of the surfaces of the nanoparticles is preferably as high as possible, but the increase in the particle size lowers the skin permeability of the nanoparticles. Accordingly, the concentration of the cationic polymer must be so designed that nanoparticles having a skin-permeable particle size (200 to 300 nm as a primary particle size before hybridization) may be constructed. For example, in case where chitosan is used as the cationic polymer, then the chitosan concentration in the poor solvent is preferably 2 mg/mL.

When the NFκB decoy-carrying nanoparticles thus produced in the manner as above is used as a starting material for a pharmaceutical preparation, then the dosage form of the carrier that contains the NFκB decoy at a high concentration in the preparation may be down-sized, and the pharmaceutical preparation of the type may have many applications for subcutaneous or intravenous injection, for transpulmonary administration, or for percutaneous or oral administration. In particular, for a percutaneous preparation for atopic dermatitis, a type of intractable diseases, the invention may bring about an epoch-making change to the current therapeutical strategy, for which, at present, steroid-based drugs that may have some side effects must be used, and the contribution of the invention to it is great.

For application to subcutaneous or intravenous injections, it is desirable that the nanoparticles are dispersed in a biocompatible buffer, for example, an aqueous solution such as Hanks' solution, Ringer solution, buffered physiological saline water, or an oily solvent such as fatty acid, e.g., sesame oil, or synthetic fatty acid, e.g., ethyl oleate, triglyceride, thereby forming water-based or oily injectable suspensions.

For percutaneous preparations, it is desirable that the nanoparticles are mixed with a base such as vaseline, lanolin, paraffin, wax, plaster, resin, plastics, higher alcohols, glycols, glycerin, optionally along with water, an emulsifier or a suspending agent added thereto, thereby forming ointments, creams, lotions or gels.

For oral preparations, it is desirable that the nanoparticles are formed into tablets along with a vehicle such as chitosan or glycoalcohol or are encapsulated into capsules, in order that the NFκB decoy held on the particle surfaces are hardly degraded by digestive enzyme.

The above-mentioned preparations may contain any other optional component than the drug component, for example, penetrant such as slime polysaccharide, phosphate, urea, phospholipid, as well as surfactant, pH controlling agent, oil or fat, water-soluble polymer, colorant, fragrance, UV absorbent, antioxidant, preservative and others, within a range within which the additives do not interfere with the effect of the invention.

In addition, the invention should not be limited to the above-mentioned embodiments, and various changes and modifications are applicable thereto; and various embodiments obtainable by suitably combining such changes or modifications with the above-illustrated techniques are also within the scope of the invention.

The pharmaceutical preparation of the invention is described more concretely with reference to the following Examples and Comparative Examples. In the following Examples and Comparative Examples, used was an NFκB decoy comprising a double stranded oligonucleotide (in the double-stranded oligonucleotide, every base-to-base bond is a phosphorothioate bond) of a sequence 5'-CCTTGAAGG-GATTTCCCTCC-3' (SEQ ID NO: 5) and its complementary sequence 5'-GGAGGGAAATCCCTTCAAGG-3' (SEQ ID NO: 6).

[Method of Preparing NFκB Decoy-Containing PLGA Nanospheres]

Example 1

50 mg of NFκB decoy was dissolved in 6 mL of purified water. One g of a biocompatible polymer, lactic acid/glycolic acid copolymer (PLGA: Wako Pure Chemical Industries' PLGA7520 (trade name); molecular weight, 20,000; lactic acid/glycolic acid molar ratio=75/25) was dissolved in 43 mL of its good solvent, acetone to prepare a polymer solution, and the above aqueous solution of NFκB decoy was added to it and mixed to prepare a liquid mixture. 5 g of an aqueous solution of 2 wt. % cationic chitosan (Moiscoat PX (trade name), by Katakura Chikkarin) was mixed in 25 mL of an aqueous solution of 2 wt. % polyvinyl alcohol (PVA:

Kuraray's Poval 403 (trade name); degree of polymerization, about 300; degree of saponification, about 80 mol %) to prepare a poor solvent. The above liquid mixture was dropwise added to the poor solvent at a constant speed (4 mL/min), with stirring at 40° C. and 400 rpm, thereby obtaining a suspension of PLGA nanospheres through diffusion of the good solvent into the poor solvent.

Subsequently, acetone was evaporated away under reduced pressure, and 20 mg of NFκB decoy was further added to the obtained suspension of nanospheres, and powdered through freeze-drying at −45° C., thereby obtaining a powder of NFκB decoy including/surface-holding PLGA nanospheres of good re-dispersibility in water, having NFκB decoy held on the surfaces of the nanospheres and having NFκB decoy included inside the nanospheres.

Example 2

30 mg of NFκB decoy was further added to the suspension of nanospheres obtained in Example 1, and powdered through freeze-drying at −45° C., thereby obtaining a powder of NFκB decoy including/surface-holding PLGA nanospheres of good re-dispersibility in water.

Example 3

A powder of NFκB decoy including/surface-holding PLGA nanospheres of good re-dispersibility in water was obtained in the same manner as in Example 1, for which, however, 60 mg of NFκB decoy was used in preparing a suspension of PLGA nanospheres.

Example 4

One g of a biocompatible polymer, lactic acid/glycolic acid copolymer (PLGA: Wako Pure Chemical Industries' PLGA7520 (trade name)) was dissolved in 43 mL of its good solvent, acetone to prepare a polymer solution, and 6 mL of pure water was added to and mixed with it to prepare a liquid mixture. 5 g of an aqueous solution of 2 wt. % cationic chitosan (Moiscoat PX (trade name), by Katakura Chikkarin) was mixed in 25 mL of an aqueous solution of 2 wt. % polyvinyl alcohol (PVA: Kuraray's Poval 403 (trade name)) to prepare a poor solvent. The above liquid mixture was dropwise added to the poor solvent at a constant speed (4 mL/min), with stirring at 40° C. and 400 rpm, thereby obtaining a suspension of PLGA nanospheres through diffusion of the good solvent into the poor solvent.

Subsequently, acetone was evaporated away under reduced pressure, and 30 mg of NFκB decoy was added to the obtained suspension of nanospheres, and powdered through freeze-drying at −45° C., thereby obtaining a powder of NFκB decoy surface-holding PLGA nanospheres of good re-dispersibility in water, having NFκB decoy held on the surfaces of the nanospheres.

Comparative Example 1

50 mg of NFκB decoy was dissolved in 6 mL of purified water. One g of a biocompatible polymer, lactic acid/glycolic acid copolymer (PLGA: Wako Pure Chemical Industries' PLGA7520 (trade name)) was dissolved in 43 mL of its good solvent, acetone to prepare a polymer solution, and the above aqueous solution of NFκB decoy was added to it and mixed to prepare a liquid mixture 25 mL of an aqueous solution of 2 wt. % polyvinyl alcohol (PVA: Kuraray's Poval 403 (trade name)) was prepared as a poor solvent. The above liquid mixture was dropwise added to the poor solvent at a constant speed (4 mL/min), with stirring at 40° C. and 400 rpm, thereby obtaining a suspension of PLGA nanospheres through diffusion of the good solvent into the poor solvent.

Subsequently, acetone was evaporated away under reduced pressure, and the excess polyvinyl alcohol was removed through centrifugation (20,000 rpm, 20 minutes), and this was powdered through freeze-drying at −45° C., thereby obtaining a powder of PLGA nanospheres of good re-dispersibility in water.

Comparative Example 2

50 mg of NFκB decoy was dissolved in 6 mL of pure water. One g of a biocompatible polymer, lactic acid/glycolic acid copolymer (PLGA: Wako Pure Chemical Industries' PLGA7520 (trade name)) was dissolved in 43 mL of its good solvent, acetone to prepare a polymer solution, and the above aqueous solution of NFκB decoy was added to it and mixed to prepare a liquid mixture. 5 g of an aqueous solution of 2 wt. % cationic chitosan (Moiscoat PX (trade name), by Katakura Chikkarin) was mixed in 25 ml of an aqueous solution of 2 wt. % polyvinyl alcohol (PVA: Kuraray's Poval 403 (trade name)) to prepare a poor solvent. The above liquid mixture was dropwise added to the poor solvent at a constant speed (4 mL/min), with stirring at 40° C. and 400 rpm, thereby obtaining a suspension of PLGA nanospheres through diffusion of the good solvent into the poor solvent.

Subsequently, acetone was evaporated away under reduced pressure, and the excess polyvinyl alcohol was removed through centrifugation (20,000 rpm, 20 minutes), and this was powdered through freeze-drying at −45° C., thereby obtaining a powder of NFκB decoy-including PLGA nanospheres of good re-dispersibility in water.

Comparative Example 3

The suspension of PLGA nanospheres obtained in Example 4 was powdered through freeze-drying at −45° C., and then a powder of NFκB decoy was uniformly mixed with it in a ratio of 2% by weight to PLGA, thereby obtaining a mixed powder of NFκB decoy and PLGA nanospheres.

Example 5

Figure 3:
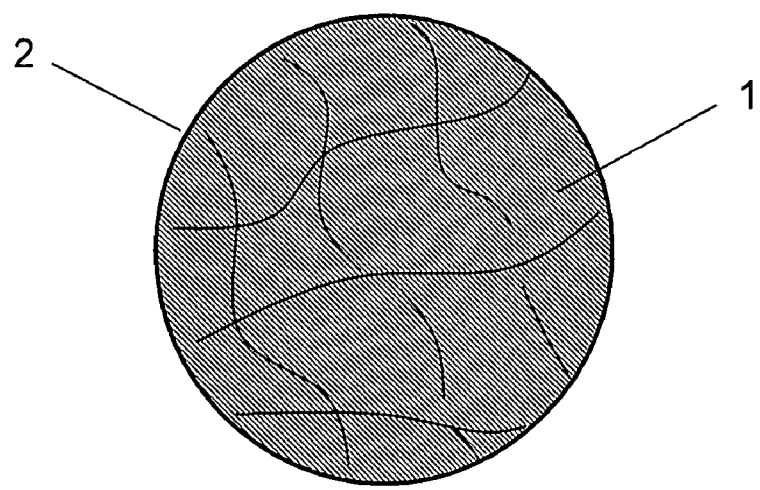
FIG. 3 is a schematic view showing a structure of the nanosphere obtained in Comparative Example 1.
Figure 4:
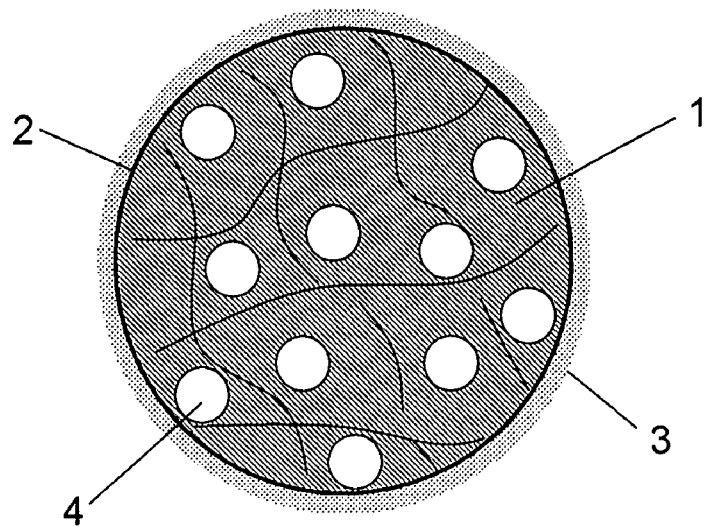
FIG. 4 is a schematic view showing a structure of the nanosphere obtained in Comparative Example 2.
Figure 5:
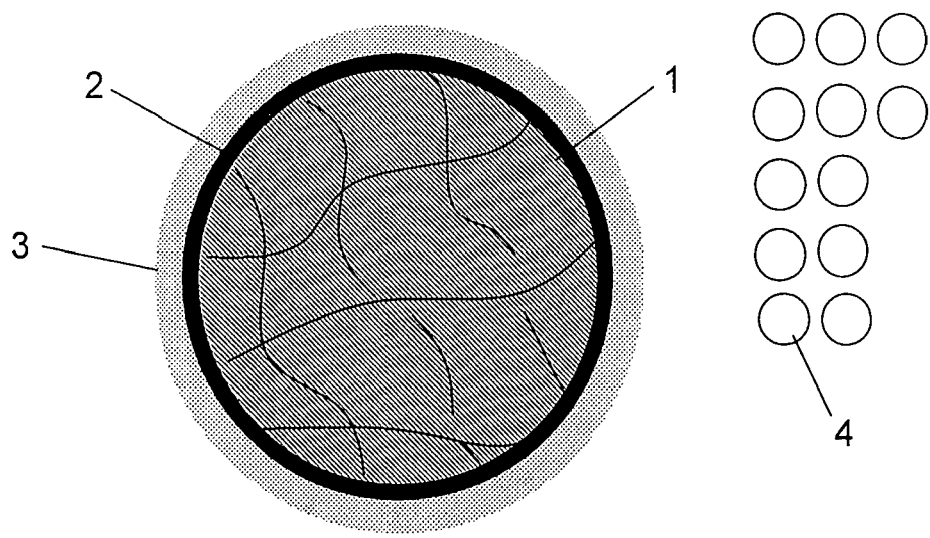
FIG. 5 is a schematic view showing a structure of the nanosphere obtained in Comparative Example 3.

The PLGA nanospheres obtained in Examples 1 to 4 and Comparative Examples 1 to 3 were re-dispersed in water, and the mean particle size thereof was measured according to a dynamic light-scattering method (device for measurement: MICROTRAC UPA (trade name) by HONEYWELL). After freeze-dried, the zeta potential of the powder surface was measured with a zeta potentiometer (ZETASIZER Nano-Z (trade name), by Malvern Instruments). Further, using a spectrophotometer (V-530 (trade name), by Nippon Bunko; wavelength for measurement, 260 nm), the NFκB decoy content in the particles (ratio by weight of NFκB decoy to PLGA nanospheres) was quantified. The measurement results are shown in Table 1. The structures of the nanospheres obtained in Comparative Examples 1 to 3 are schematically shown in FIG. 3 to FIG. 5, respectively. The structure of the nanospheres obtained in Examples 1 to 3 is shown in FIG. 2; and the structure of the nanospheres obtained in Example 4 is in FIG. 1.

TABLE 1

|  | Mean Particle Size [nm] | Zeta Potential [mV] | NFκB Decoy Content [%] (theoretical value)* |
|---|---|---|---|
| Example 1 | 355 | +46.81 | 3.5 (3.0 + 1.2) |
| Example 2 | 533 | +27.07 | 4.2 (3.0 + 1.8) |
| Example 3 | 474 | +43.07 | 5.5 (3.6 + 1.2) |
| Example 4 | 413 | +55.83 | 2.4 (1.8) |
| Comparative Example 1 | 280 | −34.16 | 0 (4.8) |
| Comparative Example 2 | 360 | +4.895 | 4.5 (4.8) |
| Comparative Example 3 | 466 | +88.11 | 1.3 (1.3) |

*Theoretical value of content (%): The amount of NFκB decoy fed in the system × 100 relative to the PLGA nanospheres is represented, as divided into (included amount + surface-held amount).

As in Table 1, the mean particle size of the freeze-dried PLGA nanospheres was 355 nm, 533 nm, 474 nm, 413 nm, 280 nm, 360 nm and 466 nm in Examples 1 to 4 and Comparative Examples 1 to 3, respectively, in that order, and it was distributed within a range of from about 280 nm to 530 nm.

The zeta potential on the nanosphere surfaces in Examples 1 to 4 and Comparative Examples 2 and 3 in which chitosan was added to the poor solvent was +46.81 mV, +27.07 mV, +43.07 mV, mV, +4.895 mV and +88.11 mV, respectively; and the particle surfaces were plus-charged. It is presumed that the reason why the zeta potential in Comparative Example 2 is lower than that in the others will be because chitosan on the particle surfaces would be removed along with polyvinyl alcohol in centrifugation. On the other hand, the zeta potential on the nanosphere surfaces in Comparative Example 1 in which chitosan was not added to the poor solvent was −34.16 mV, and the particle surfaces were minus-charged.

In the nanospheres in Examples 1 to 4 and Comparative Example 2, the NFκB decoy content was 3.5%, 4.2%, 5.5%, 2.4%, and 4.5%, respectively; and in these, the inclusion percentage was comparable to or more than the theoretical value thereof. This would be because the cationic polymer (chitosan) 3 adsorbed by the surface of the nanoparticle 1 made it possible to electrostatically hold the NFκB decoy 4 thereon and additionally made it possible to include the NFκB decoy 4 inside the nanosphere while preventing it from leaking out into the poor solvent (see FIG. 1, FIG. 2, FIG. 4).

In Examples 1 to 3, the theoretical value (3.0% and 3.6%) of the NFκB decoy content included inside the particles is lower than that (4.8%) in Comparative Example 2, and this is because in Examples 1 to 3, the system was not subjected to centrifugation and therefore the amount of chitosan and polyvinyl alcohol adhering to the particle surfaces was larger than in Comparative Example 2, therefore resulting in that the total weight of the PLGA nanospheres that is to be the denominator in computing the content is larger in these.

On the other hand, in the nanospheres in Comparative Example 1 in which chitosan was not added to the poor solvent, NFκB decoy was not almost included inside the particles. From the result, it is presumed that in Comparative Example 1, the water-soluble NFκB decoy would have leaked out into the outer phase, poor solvent with the result that only PLGA deposited to form nanospheres, as in FIG. 3.

[NFκB Decoy Release Test (In Vitro) from NFκB Decoy-Containing PLGA Nanospheres]

Example 6

500 mg of NFκB decoy-including/surface-holding PLGA nanospheres (mean particle size 469 nm, NFκB decoy content 5.4%) prepared in the same manner as in Example 1, and NFκB decoy-including PLGA nanospheres (mean particle size 316 nm, NFκB decoy content 3.4%) prepared in the same manner as in Comparative Example 2 were weighed, and each portion was dispersed in 50 mL of physiological saline water. The dispersion was stirred in a warm water bath at 32±0.5° C. Next, this was sampled to take samples of 5 mL each at predetermined intervals, and 100 μl of aqueous 10 N NaOH solution was added thereto, and filtered through a membrane filter (0.2 μm). 1 mL of the filtrate was made up to 10 mL with aqueous 3.3 M NaCl solution (aqueous 10 N NaOH solution to make pH of 12). This was analyzed with a spectrophotometer (V-530 (trade name), by Nippon Bunko), and based on the absorption at a wavelength of 260 nm at which the obtained absorption waveform had a peak top, the NFκB decoy release amount and release percentage was computed. The results are shown in FIG. 6.

Figure 6:
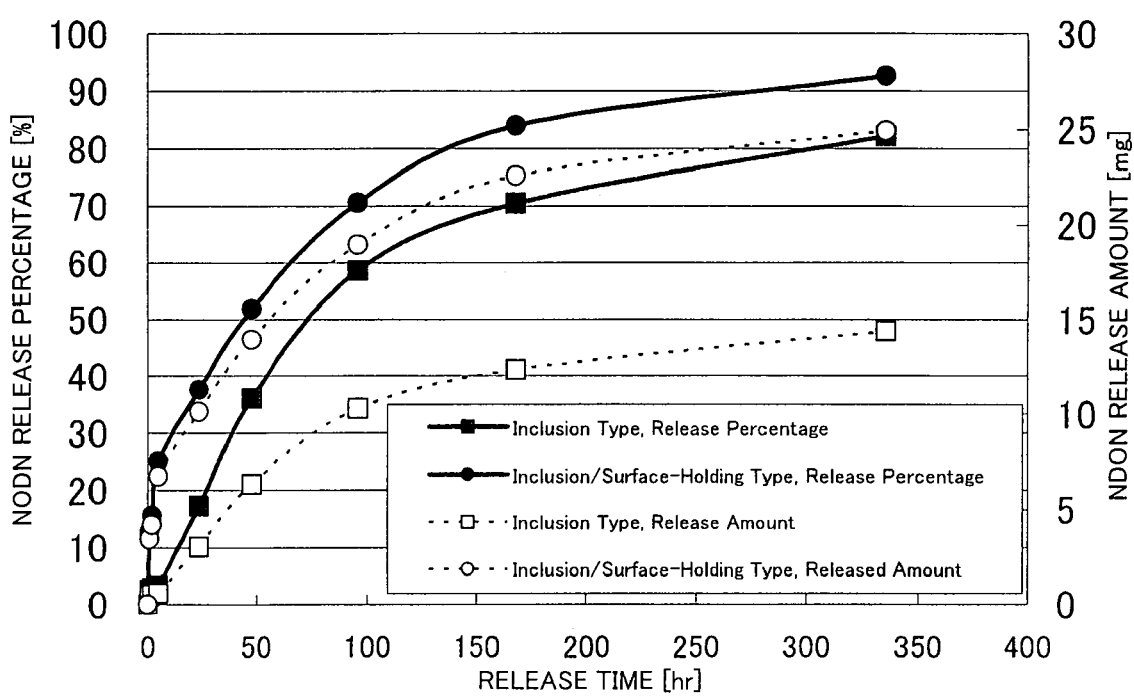
FIG. 6 is a graph showing an NFκB decoy release (NODN) profile from NFκB decoy-including/surface-holding nanospheres and NFκB decoy-including nanospheres.

As is obvious from FIG. 6, the NFκB decoy release amount from the NFκB decoy-including/surface-holding PLGA nanospheres in 4 hours after the dispersion was about 7 mg, and the release percentage was about 30%. From this, it is presumed that the NFκB decoy held on the surfaces of the particles were released in the initial stage within 4 hours after administration and thereafter the NFκB decoy included inside the particles were gradually released. On the other hand, the NFκB decoy release percentage from the NFκB decoy-including PLGA nanospheres in 4 hours was at most 5%.

In 4 days (in 96 hours) after the dispersion, the NFκB decoy release amount from the NFκB decoy-including/surface-holding PLGA nanospheres was about 19 mg, and that from the NFκB decoy-including PLGA nanospheres was about 10 mg, and the release percentage from these was more than 50% each. In 7 days (in 168 hours), the NFκB decoy release amount from the NFκB decoy-including/surface-holding PLGA nanospheres was about 23 mg, and that from the NFκB decoy-including PLGA nanospheres was about 13 mg, and the release percentage from these was more than 70% each. The results confirm that the NFκB decoy-including/surface-holding PLGA nanospheres are more advantageous in point of the quick-acting potency thereof, as compared with the NFκB decoy-including PLGA nanospheres.

[Test for Assessment of Potency (In Vivo) of NFκB Decoy-Containing PLGA Nanospheres with Ovalbumin Induced Delayed type Allergy Model]

The PLGA nanospheres prepared in Examples 1 to 4 and Comparative Examples 1 to 3 were tested for their inhibitory effect to an OVA induced delayed type allergy (delayed type hypersensitivity, DTH) model, using ovalbumin (egg albumin, hereinafter referred to as "OVA") as a sensitizer. The test method is described below.

Example 7

Preparation of Drug Sample

A predetermined amount of the PLGA nanospheres obtained in Examples 1 and 2 were weighed and dispersed in a small amount of pure water, and then mixed with white vaseline so that the water content of the resulting preparation could be 30%, thereby preparing three types of PLGA nanospheres-containing creams having an NFκB decoy content of 0.05%, 0.15% or 0.5%. For control, prepared were a vaseline ointment having an NFκB decoy content of 2% (positive control), and a vaseline ointment with no NFκB decoy (negative control).

(Test for DTH Reaction Inhibitory Potency)

In an ordinary assessment method, in general, a sample to be tested is administered on the day before secondary sensitization, and the immune system-relaxing effect of the test sample in the test model to the sensitizer in secondary sensitization, or that is, the allergy reaction-inhibiting effect thereof to the once-formed antibody is assessed. In this, however, the sample to be tested is administered on the day before primary sensitization, and the effect of the sample to prevent the receptor cells from recognizing OVA as an antigen in the pre-stage of allergy reaction, is assessed.

The cream or the ointment was applied to the abdominal area of each BALB/c mouse (7-week age, female, by Nippon Clea) in an amount of 10 mg/head (n=15 in each test group). After one day, physiological saline water containing 5 mg/mL of OVA was subcutaneously injected in 2 sites of the abdominal area, in an amount of 100 µL each (primary sensitization).

Eight days after the OVA administration, 50 µL of physiological saline water containing 2 mg/mL of OVA was subcutaneously injected onto the sole of the right back paw of each mouse (secondary sensitization). On the other hand, 50 µL of PBS (phosphate buffer) was administered onto the sole of the left back paw thereof. Mice with neither primary sensitization nor secondary sensitization were in a normal group (control group n=15). After one day, the sole thickness of the right back paw and that of the left back paw were measured with calipers, and the difference between the two is the DTH reaction to OVA. The mean value of the difference between the sole thicknesses was computed and statistically processed in each of the test groups and the control group, and the test compound was assessed for its effect to inhibit DTH reaction.

The significant difference test is as follows: Wilcoxson test favorable for a difference between two groups was applied to the significant difference between the vaseline ointment with no NFκB decoy (negative control) and the 2% NFκB decoy-containing vaseline ointment (positive control); and Dunnett test capable of detecting a significant difference with a concentration difference added relative to the control, was applied to the significant difference between three types of PLGA nanospheres-containing creams having an NFκB decoy concentration of 0.05%, 0.15% and 0.5%. The results are shown in FIG. 7 and FIG. 8.

Figure 7:
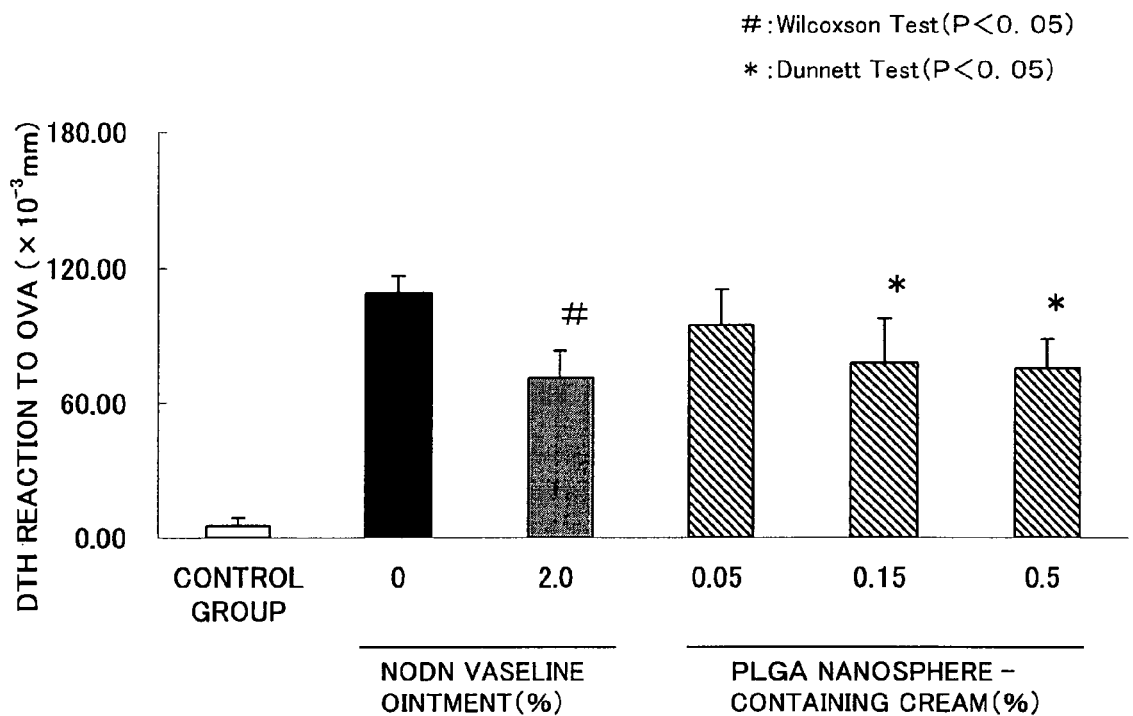
FIG. 7 is a graph showing an OVA induced delayed type allergy inhibiting effect of the nanospheres of Example 1.

As is obvious from FIG. 7, in the case where the NFκB decoy-including/surface-holding PLGA nanospheres-containing cream of Example 1 was applied to the mice of the groups in which the cream has an NFκB decoy content of 0.05%, 0.15% or 0.5%, the difference in the sole thickness between the right back paw and the left back paw was $95 \times 10^{-3}$ mm, $75 \times 10^{-3}$ mm and $70 \times 10^{-3}$ mm, respectively; and the DTH reaction in the mice of those groups was inhibited, as compared with that in the mice of the group to which the NFκB decoy-free vaseline ointment was applied ($110 \times 10^{-3}$ mm). In particular, in the groups where the cream having an NFκB decoy content of 0.15% or 0.5% was applied, a significant inhibition was admitted to the same level as that of the mice of the group where 2% NFκB decoy-containing vaseline ointment was applied ($70 \times 10^{-3}$ mm) ($p<0.05$).

Figure 8:
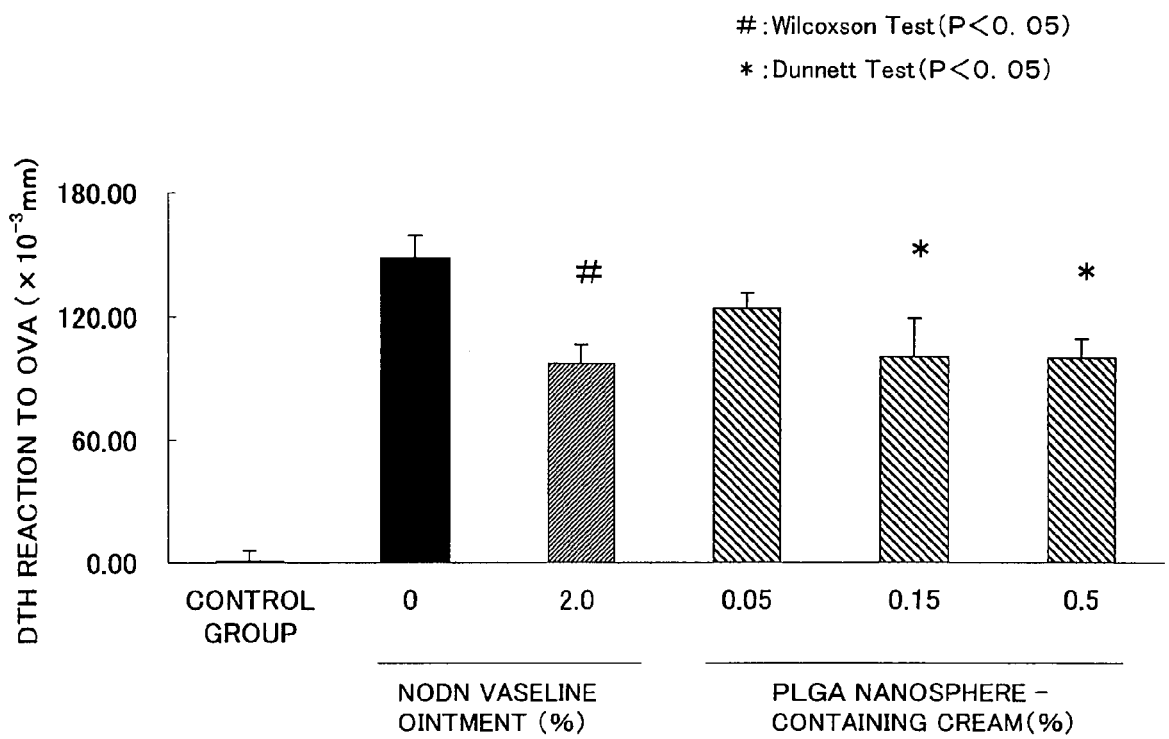
FIG. 8 is a graph showing an OVA induced delayed type allergy inhibiting effect of the nanospheres of Example 2.

Also as in FIG. 8 indicating the test results with the PLGA nanospheres-containing cream of Example 2 in which the surface-held NFκB decoy amount was larger than that in Example 1, in the groups where the cream having an NFκB decoy content of 0.05%, 0.15% or 0.5%, the difference in the sole thickness between the right back paw and the left back paw was $120 \times 10^{-3}$ mm, $105 \times 10^{-3}$ mm and $100 \times 10^{-3}$ mm, respectively; and the DTH reaction in the mice of those groups was inhibited, as compared with that in the mice of the group to which the NFκB decoy-free vaseline ointment was applied ($150 \times 10^{-3}$ mm). In particular, in the groups where the cream having an NFκB decoy content of 0.15% or 0.5% was applied, a significant inhibition was admitted to the same level as that of the mice of the group where 2% NFκB decoy-containing vaseline ointment was applied ($90 \times 10^{-3}$ mm) ($p<0.05$).

The results confirm the effectiveness of the NFκB decoy-including/surface-holding PLGA nanospheres-containing cream even at a low dose, or that is, even though its dose is about 1/10 of the ointment that contains the NFκB decoy as it is, the cream is still effective to the same level as that of the ointment. This may be because the PLGA nanospheres may act as a carrier, and the NFκB decoy intake efficiency into cells could increase by about 10 times.

Example 8

Using the PLGA nanospheres obtained in Examples 3 and 4 and Comparative Examples 1 to 3, PLGA nanospheres-containing creams having an NFκB decoy content of 0.5% were prepared in the same manner as in Example 7. Also in the same manner as in Example 7, the creams were tested for the effect of inhibiting DTH reaction to OVA. Since the samples tested all had one and the same NFκB decoy concentration of 0.5%, herein employed is Wilcoxson test favorable for determining a significant difference between two groups. The results are shown in FIG. 9.

Figure 9:
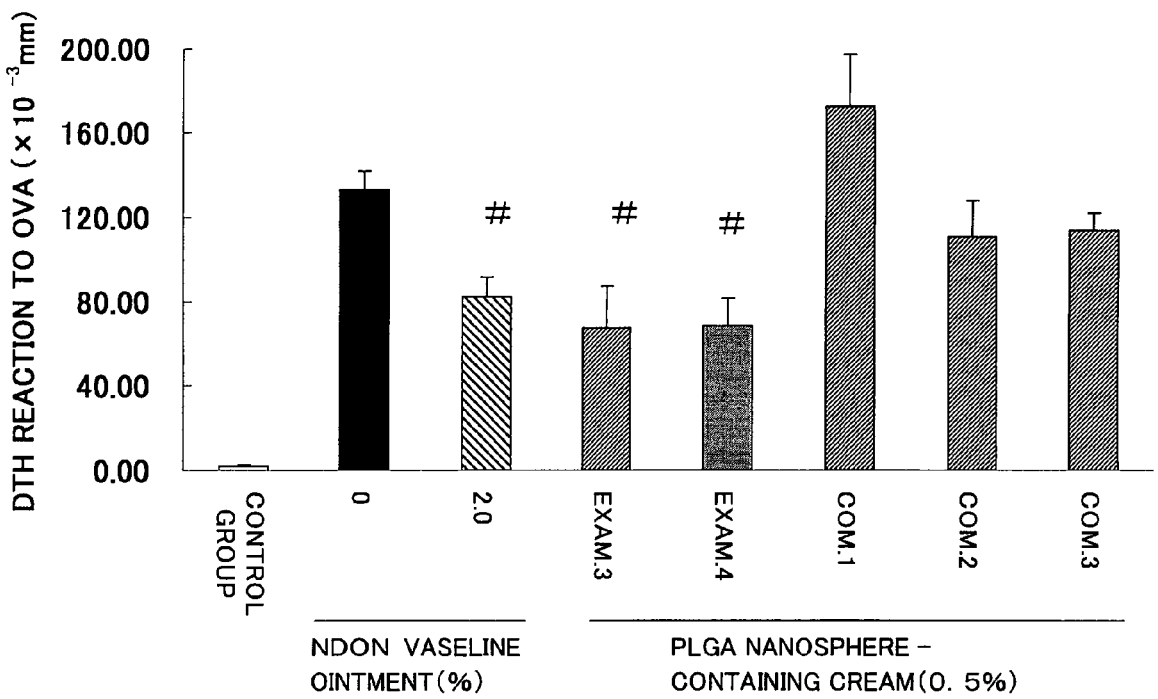
FIG. 9 is a graph showing an OVA induced delayed type allergy inhibiting effect of the nanospheres of Examples 3, 4 and Comparative Examples 1 to 3.

As is obvious from FIG. 9, in the case where the PLGA nanospheres-containing cream of Example 3 in which the surface-held NFκB decoy amount was reduced and the included NFκB decoy amount was increased, or that of Example 4 in which the NFκB decoy was held only on the sphere surfaces was applied, the sole thickness difference was $70 \times 10^{-3}$ mm each, and in those groups, the DTH reaction was significantly inhibited to the same level ($80 \times 10^{-3}$ mm) as that in the group to which 2% NFκB decoy-containing vaseline ointment was applied ($p<0.05$).

On the other hand, in the case where the NFκB decoy-including PLGA nanospheres-containing cream of Comparative Example 2 was applied to the mice, the sole thickness difference was $110 \times 10^{-3}$ mm, and the DTH reaction was inhibited in these mice as compared with that in the group where the NFκB decoy-free vaseline ointment was applied ($130 \times 10^{-3}$ mm); but as compared with that in the group where the 2% NFκB decoy-containing vaseline ointment was applied ($80 \times 10^{-3}$ mm), the inhibiting effect of the cream was low, and the reduction in the effective dose of the cream was not admitted.

In Example 6, the NFκB decoy release percentage in 24 hours from the NFκB decoy-including/surface-holding PLGA nanospheres reached 40%; however, it was less than 20% from the NFκB decoy-including PLGA nanospheres (see FIG. 6). Taking this into consideration, it may be presumed that, in Examples 3 and 4 where NFκB decoy was held on the surfaces of PLGA nanospheres and the PLGA nanospheres-containing creams were applied to the mice, the NFκB decoy held on the nanosphere surfaces was released out within a short period of time after the cream administration and contributed to the quick action of the creams.

In the case where the PLGA nanospheres-containing cream of Comparative Example 3, which had been prepared by mixing NFκB decoy-free PLGA nanospheres and NFκB decoy powder, was applied to the mice, the sole thickness difference was $110 \times 10^{-3}$ mm; and its inhibiting effect was low as compared with that in the 2% NFκB decoy-containing vaseline ointment application group ($80 \times 10^{-3}$ mm). This may be because, since the power of the surface of the nanosphere 1 to adsorb the NFκB decoy 4 was weak as in FIG. 5, the NFκB decoy 4 could not penetrate through the skin along with the nanosphere 1 to sufficiently reach the inside of cells.

In the case where the NFκB decoy-free PLGA nanospheres-containing cream of Comparative Example 1 was applied, the sole thickness difference was 170×0-3 mm, and the effect of the cream to inhibit DTH reaction could not be admitted. The result confirms that PLGA itself does not have the inhibiting effect.

The pharmaceutical preparation of the invention comprises biocompatible nanoparticles of which the zeta potential of the surface is made positive by the cationic polymer applied thereto and which therefore electrostatically hold NFκB decoy on their surfaces, and it has high penetrability into living bodies and has high NFκB decoy delivery efficiency into the inside of cells. Since the NFκB decoy may be released out in a short period of time after the administration thereof, the pharmaceutical preparation is advantageous in point of its quick action expressibility. Accordingly, even when the preparation is applied to a site having a high barrier function, the NFκB decoy therein may be rapidly and sufficiently delivered to the inside of the cells in the affected site, and therefore, the preparation may be expected as an effective therapeutical medicine for an intractable diseases, atopic dermatitis.

When the nanoparticles are made to include NFκB decoy inside them, the NFκB decoy content of the preparation may be further increased, and the preparation may be down-sized, and in addition, it may satisfy both quick-acting capability and sustainability. Further, when chitosan or a chitosan derivative is used as the cationic polymer and when any of polylactic acid, polyglycolic acid or PLGA is used as the biocompatible polymer, then the pharmaceutical preparation may be highly safe and may have excellent stability and sustainability.

The complete disclosure of each document identified hereinbelow in the List of References is incorporated herein by reference.

LIST OF REFERENCES

1 Japanese Patent No. 3778357
2 JP-A 2005-306877
3 JP-A 2006-89475
4 JP-T-Re 2003/099339
5 JP-A 2006-111591
6 Dictionary of Molecular and Cellular Biology (published by Tokyo Kagaku Dojin, 1997)

What is claimed is:

1. A pharmaceutical preparation containing biocompatible polymer nanoparticles that are coated with a cationic polymer on their surfaces and have an NF$_k$B decoy oligonucleotide absorbed and held thereon, wherein the NF$_k$B decoy oligonucleotide is further included inside the nanoparticles.

2. The pharmaceutical preparation as claimed in claim 1, wherein the nanoparticles are hybridized with a binder and the NF$_k$B decoy oligonucleotide is further included inside the outer layer formed of the binder.

3. The pharmaceutical preparation as claimed in claim 1, wherein the cationic polymer is chitosan or a chitosan derivative.

4. The pharmaceutical preparation as claimed in claim 1, wherein the biocompatible polymer is any of a polylactic acid, a polyglycolic acid or a lactic acid/glycolic acid copolymer.

5. The pharmaceutical preparation as claimed in claim 1, wherein the NF$_k$B decoy oligonucleotide includes an NF$_k$B binding sequence represented by the following SEQ ID NO: 1:

[G]nGGRHTYYHC    (SEQ ID NO: 1)

wherein n indicates 0 or 1; R means A or G; Y means C or T; H means A, C or T.

6. The pharmaceutical preparation as claimed in claim 5, wherein the NF$_k$B decoy oligonucleotide includes at least one of GGGATTTCCC (SEQ ID NO: 2), GGGACTTTCC (SEQ ID NO: 3) or GGACTTTCC (SEQ ID NO: 4), as the NF$_k$B-binding sequence.

7. The pharmaceutical preparation as claimed in claim 6, wherein the NF$_k$B decoy oligonucleotide is a double-standed oligonucleotide comprising a sequence 5'-CCTTGAAGG-GATTTCCCTCC-3' (SEQ ID NO: 5) and a sequence complementary to it, 5'-GGAGGGAAATCCCTTCAAGG-3' (SEQ ID NO: 6).

8. The pharmaceutical preparation as claimed in claim 1, wherein the content of the NF$_k$B decoy oligonucleotide in the nanoparticles is from 0.5% by weight to 30% by weight.

9. The pharmaceutical preparation as claimed in claim 1, wherein the nanoparticles have a mean particle size of from 10 nm to 1,000 nm.

10. The pharmaceutical preparation as claimed in claim 9, wherein the nanoparticles have a mean particle size of from 50 nm to 300 nm.

11. The pharmaceutical preparation as claimed in claim 1, which is used for treatment of skin diseases.

12. The pharmaceutical preparation as claimed in claim 11, wherein the skin disease is atopic dermatitis.

* * * * *

UNITED STATES PATENT AND TRADEMARK OFFICE
CERTIFICATE OF CORRECTION

PATENT NO.        : 7,897,751 B2
APPLICATION NO.   : 11/812459
DATED             : March 1, 2011
INVENTOR(S)       : Yusuke Tsukada et al.

It is certified that error appears in the above-identified patent and that said Letters Patent is hereby corrected as shown below:

On the title page, Item (73)

Assignee: please add ANGES MG, INC. as a co-assignee.

Signed and Sealed this
Twenty-fourth Day of January, 2012

David J. Kappos
*Director of the United States Patent and Trademark Office*

```
                        SEQUENCE LISTING

<160> NUMBER OF SEQ ID NOS: 10

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: May or may not be present

<400> SEQUENCE: 1 gggrhtyyhc                                                            10

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gggatttccc                                                            10

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gggactttcc                                                            10

<210> SEQ ID NO 4
```

```
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4 ggactttcc                                                                 9

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ccttgaaggg atttccctcc                                                    20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggagggaaat cccttcaagg                                                    20

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      oligoneotide

<400> SEQUENCE: 7
agttgaggac tttccaggc                                                     19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gcctggaaag tcctcaact                                                     19

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
agttgagggg actttcccag gc                                                 22

<210> SEQ ID NO 10
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 10
gcctgggaaa gtccctcaa ct                                              22
```